United States Patent [19]

Trijzelaar et al.

[11] 4,443,453
[45] Apr. 17, 1984

[54] QUINOLINE DERIVATIVES, PHARMACEUTICAL COMPOSITIONS CONTAINING SUCH COMPOUNDS, AND METHODS FOR TREATING CARDIOVASCULAR CONDITIONS WITH THEM

[75] Inventors: Hans B. Trijzelaar, Zeist; Ronus de Bode, Bilthoven; Handricus B. A. Welle, Maarssen, all of Netherlands

[73] Assignee: ACF Chemiefarma N.V., Netherlands

[21] Appl. No.: 240,817

[22] Filed: Mar. 5, 1981

[30] Foreign Application Priority Data

Mar. 6, 1980 [NL] Netherlands ................ 8001369
Jul. 11, 1980 [NL] Netherlands ................ 8004002

[51] Int. Cl.$^3$ ................ A61K 31/47; C07D 401/06
[52] U.S. Cl. ................ 424/258; 546/168; 546/174; 546/176; 546/177
[58] Field of Search ........... 546/156, 157, 176, 177, 546/168, 174; 424/258

[56] References Cited

U.S. PATENT DOCUMENTS

| | | | |
|---|---|---|---|
| 3,914,235 | 10/1975 | Gutzwiller et al. | 424/258 X |
| 3,953,453 | 4/1976 | Grethe et al. | 546/134 |
| 4,237,139 | 12/1980 | Champseix et al. | 424/258 |
| 4,238,612 | 12/1980 | Barieux et al. | 546/153 |
| 4,299,835 | 11/1981 | Champseix et al. | 424/258 |
| 4,402,961 | 9/1983 | Dubroeucq et al. | 424/258 |

FOREIGN PATENT DOCUMENTS

2315148 10/1973 Fed. Rep. of Germany .
2206944 6/1974 France ................ 546/176

OTHER PUBLICATIONS

Grethe, et al., Chemical Abstracts, vol. 83, 114,718j (1975).
Heidelberger, et al., J. Am. Chem. Soc., vol. 44, pp. 1098-1107 (1922).
Wirth, Chemical Abstracts, vol. 76, 103776f (1972).
Wirth, Chemical Abstracts, vol. 80, 124762w (1974).
Dawes, British J. Pharmacol., 1, pp. 90-111 (1946).

*Primary Examiner*—Donald G. Daus
*Assistant Examiner*—Diana G. Rivers
*Attorney, Agent, or Firm*—Jacobs & Jacobs

[57] ABSTRACT

The invention is concerned with novel quinoline derivatives of the formula

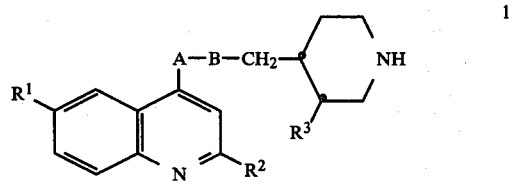

or a salt thereof, in which A—B is —CH$_2$—CH$_2$—, —CHOH—CH$_2$—, —CH$_2$—CHOH—, —CH$_2$—C(O)—, —C(NOR$^4$)—CH$_2$— or —CH$_2$—C(NOR$^4$)—, R$^1$ is hydrogen, hydroxy or lower alkoxy, R$^2$ is lower alkyl, R$^3$ is ethyl or vinyl, R$^4$ is lower alkyl, whereby the substituents at the 3- and 4-position of the piperidine ring are in the cis-position. The compounds of the formula may be in the form of the optically active enantiomers and/or their therapeutically acceptable salts. Furthermore the invention provides pharmaceutical compositions possessing cardiovascular activities in which as active compound at least a compound of the above formula is used. Methods for the preparation of the pharmaceutical compositions and of the active compounds are also included by the invention.

4 Claims, No Drawings

QUINOLINE DERIVATIVES, PHARMACEUTICAL COMPOSITIONS CONTAINING SUCH COMPOUNDS, AND METHODS FOR TREATING CARDIOVASCULAR CONDITIONS WITH THEM

The invention relates to quinoline derivatives and pharmaceutical compositions containing such compounds.

In French Pat. No. 73,41043 (Publ. No. 2,206,944) quinoline derivatives of the formula: are described,

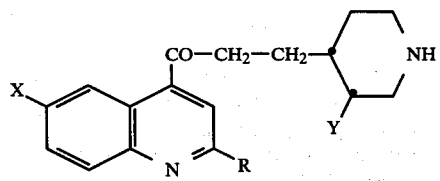

in which X is hydrogen or methoxy, Y is hydrogen, ethyl or vinyl and R is $C_{1-4}$ alkyl, cycloalkyl or optionally substituted aralkyl or aryl, which compounds may be used for the treatment and prophylaxis of cardiovascular affections.

From Ann. Pharm. Fr. 24, 39 (1966) the pharmacodynamic properties of quinicine, which chemically is 1-(6-methoxy-4-quinolyl)-3-(3-vinyl-4-piperidyl)-1-propanone also named viquidil, are known, in particular in the field of CNS, and the hypotensive, vasodilative and anti-spasmodic activities.

In British Pat. No. 1,294,538 the use of viquidil in the treatment of cerebral vessel injury, cerebrovascular insufficiency and memory deficiency in humans is described.

In Dutch Patent Application No. 77,06614 quinoline derivatives are described of the formula:

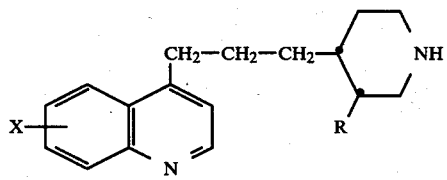

in which R is hydrogen, $C_{1-4}$ alkyl or $C_{2-4}$ alkenyl and X is hydrogen, halogen, $C_{1-4}$ alkyl, alkoxy or alkylthio, trifluoromethyl, nitro, hydroxy, an amino group optionally substituted by one or two $C_{1-4}$ alkyl groups, or $C_{1-4}$ acyl or alkylsulfonyl group, which compounds have a serotonin uptake inhibiting effect and anti-arrhythmic activity.

In German patent application DT 2,949,993 the use of compounds of the formula:

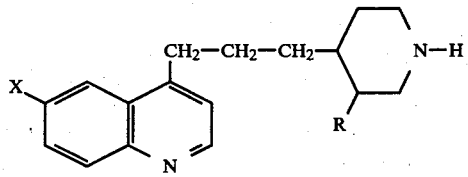

with R and X are both H; or R is vinyl or ethyl; and X is H or methoxy; is claimed for treatment of anxiety.

In U.S. Pat. Nos. 3,873,549 and 3,914,235 compounds of the formula:

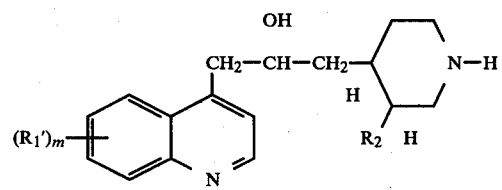

and their antipodes and racemates, where m=0, 1 or 2; $R_1'$=OH, halogen, $CF_3$, methyl, ethyl, propyl, butyl or methoxy or, when m is 2, $R_1'$ with an adjacent $R_1'$ may also be methylenedioxy; and $R_2$ is vinyl or ethyl, are described as intermediates for quinine and quinidine compounds of known use as anti-malarials and anti-arrhythmics, whereas such compounds showed bactericidal activity.

It has now been found, that quinoline derivatives substituted at the 2- and 4-position and optionally at the 6-position, and in which the substituent at the 4-position contains a 3,4-disubstituted piperidyl group, possess unexpected pharmacological properties, namely desirable effects on the cardiovascular system such as antihypertensive, anti-thrombotic, vasodilatory and anti-arrhythmic activity. The compounds are particularly useful in medicines administered for the treatment of hypertensive or arrhythmic conditions.

Thus, the invention provides compounds of formula 1,

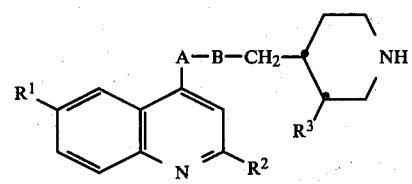

in which
A—B is —$CH_2$—$CH_2$—, —CHOH—$CH_2$—, —$CH_2$—CHOH—, —$CH_2$—C(O)—, —C(NOR$^4$)—$CH_2$— or —$CH_2$—C(NOR$^4$)—,
$R^1$ is hydrogen, hydroxy or lower alkoxy,
$R^2$ is lower alkyl,
$R^3$ is ethyl or vinyl,
$R^4$ is lower alkyl,
whereby the substituents at the 3- and 4-position of the piperidine ring are in the cis configuration, and acid addition salts thereof.

As is usual, the carbon chains of the different groups may be straight or branched.

The term "lower" is here used to mean a group with up to six carbon atoms.

Suitably, A—B is —$CH_2$—$CH_2$—. Another suitable meaning of A—B is —CHOH—$CH_2$—. Also suitable is the meaning of A—B being —$CH_2$—CHOH—. Suitably, A—B is —$CH_2$—C(O)—. The meaning of A—B being —C(NOR$^4$)—$CH_2$ is also apt, as well as A—B being —$CH_2$—C(NOR$^4$)—, $R^4$ is being preferably methyl.

Where $R^1$ is alkoxy, it is preferably methoxy. $R^1$ is preferably hydrogen or methoxy. Favourably $R^1$ is hydrogen. Also favourably $R^1$ is methoxy.

Suitable values for $R^2$ include methyl, ethyl, n- and iso-propyl, n- and iso-butyl, n-pentyl and n-hexyl. Preferably, $R^2$ is methyl or n-propyl.

Our copending application Ser. No. 240,808 filed Mar. 5, 1981 describes compounds of the formula:

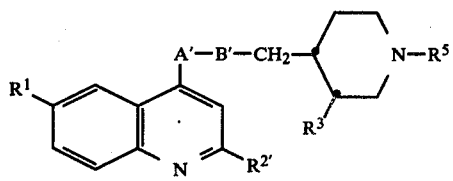

in which $R^1$ and $R^3$ have the same meanings as the compounds of formula 1, A'—B' is as defined as A—B in formula 1 and may also have the meaning of —C(O)—CH$_2$—, $R^{2'}$ is lower alkyl, hydroxy or lower alkoxy and $R^5$ is a substituent other than hydrogen, which compounds possess certain cardiovascular properties.

A particular group of compounds of formula 1 are those of formula 1a,

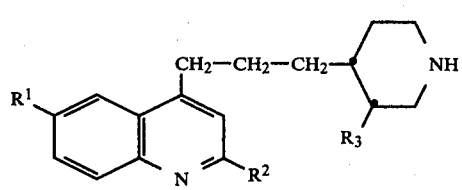

in which $R^1$, $R^2$ and $R^3$ are as previously defined. Preferably, $R^1$ is hydrogen, $R^2$ is methyl and $R^3$ is ethyl.

Another group of compounds of formula 1 are those of formula 1b,

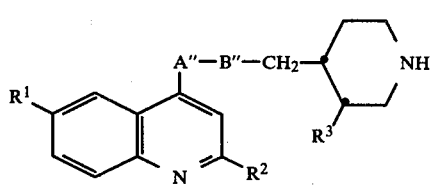

in which A"—B" is —C(NOR$^4$)—CH$_2$— or —CH$_2$—C(NOR$^4$)— and $R^1$, $R^2$, $R^3$ and $R^4$ are as previously defined. Preferably, $R^2$ is methyl, $R^3$ is ethyl and $R^4$ is methyl. Especially preferred is the compound in which A—B is —C(NOCH$_3$)—CH$_2$—, $R^1$ is hydrogen, $R^2$ is methyl and $R^3$ is ethyl.

Another group of compounds of formula 1 are those of formula 1c,

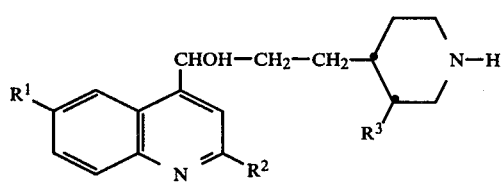

in which $R^1$, $R^2$ and $R^3$ are as defined for the compounds of formula 1.

The preceding compounds of formula 1 may exist in free base form or in the form of their acid addition salts, for example their salts with mineral acids, e.g. hydrochloric acid, hydrobromic acid or sulphuric acid, or organic acids e.g. acetic acid, fumaric acid or tartaric acid. Naturally the acid used will be pharmaceutically acceptable when such salts are intended for internal administration.

The compounds of formula 1 in which A or B is —CHOH— contain an asymmetric carbon atom and therefore two diastereoisomers may exist, provided that there are no asymmetric carbon atoms in a side chain.

The compounds of the invention are obtainable in crystalline form. They may also be obtained in the form of solvates such as hydrates.

The compounds of the invention, as represented by formula 1, include free base and acid addition salt forms, mixtures of diastereoisomers and separated forms thereof.

The compounds of formula 1 may be prepared in most cases according to methods known for the preparation of analogous compounds.

In the above-cited French Pat. No. 73,41043 the preparation is described, according to two different methods, of compounds in which X is hydrogen or methoxy, Y is among other things ethyl and vinyl and R is among other things C$_{1-4}$ alkyl. The starting material in the first method is a suitable cinchona alkaloid, such as quinine, cinchonine or the hydroderivatives of these compounds, which is converted into the corresponding ar-mono-N-oxide in a manner known per se, which compound is then converted with a lithium or Grignard compound into a cinchona alkaloid substituted at the 2'-position by alkyl (or cycloalkyl, aralkyl or aryl).

The resulting compounds are converted in conventional manner into the so-called open compounds of formula 2 by reacting with moderately diluted acid at elevated temperature.

The second method described in said French patent is based on the condensation of an ester of 3-(4-piperidyl) propionic acid with a quinoline derivative, which is substituted at the 4-position by a carboxylic ester group or a lithium atom.

In J. Amer. Chem. Soc. 100, 576-581 (1978) the preparation of 1-(6-methoxy-4-quinolyl)-3-(3-vinyl-4-piperidyl-2-propanone is described by converting 6-methoxylepidine in situ of 6-methoxylepidyllithium and reacting this compound with the methyl ester of a 4-piperidyl acetic acid derivative (N-benzoylmeroquinene methyl ester). While removing the N-benzoyl group of the resulting keto compound of the 1,3-disubstituted propanone-2 type, the compound is reduced to a propanol-2 derivative.

The compounds of formula 1, in which A—B is —CH$_2$—CH$_2$— or CHOH—CH$_2$—, may be advantageously obtained by complete or partial reduction, respectively, of the corresponding compound in which A—B is —C(O)—CH$_2$. A suitable reducing agent for the conversion to the desoxo compound (—CH$_2$—CH$_2$—) is e.g. hydrazine hydrate, in the presence of an alkali metal hydroxide, such as potassium hydroxide, in a suitable solvent such as an alcohol, e.g. ethylene glycol. A suitable reducing agent for the partial reduction to the alcohol derivative (—CHOH—CH$_2$—) is for example a complex hydride, such as sodium borohydride. This reduction is advantageously carried out at a temperature of about $-5°$ to $-10°$ C. in a suitable solvent, like an alcohol, e.g. isopropyl-alcohol. If desired, the alcohol compound may also be converted into the corresponding desoxo compound, e.g. by converting the alcohol in a suitable solvent, such as tetrachloromethane with phosphorus pentachloride to the chloride and reducing the resulting compound, for example with hydrogen gas in a solvent, such as ethylalcohol and for example palladium on coal as a catalyst.

The starting compound (a compound of formula 1, in which A—B is —C(O)—CH₂—), which may be used for the preparation of the said compounds of formula 1 according to the invention, may be advantageously prepared in a way analogous to the first method of the French Patent, starting from compounds of the formula:

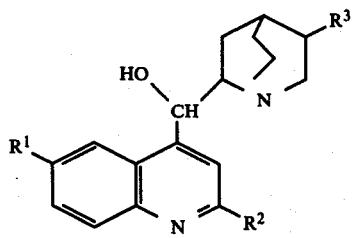

2 in which $R^1$, $R^2$ and $R^3$ are as defined before. The hydramine splitting of the cinchona alkaloid, which is substituted at the 2'-position by alkyl, to a compound of formula 1 defined above, is preferably carried out with moderately diluted acetic acid or sulphuric acid, preferably at a temperature of about 100° C. to the boiling point of the mixture.

The 2'-unsubstituted ar-mono-N-oxide compounds of the formula:

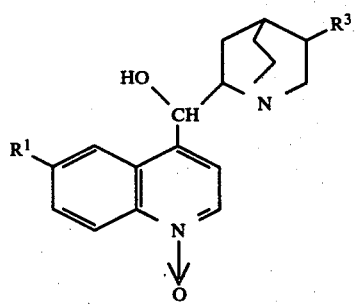

3 in which $R^1$ and $R^3$ have the meanings as mentioned before, to be used for the reaction, are known or they may be prepared by an analogous method from known compounds. From the on the 2'-position unsubstituted cinchona alkaloid, which is used as starting compound, the 6'-position is preferably unsubstituted or substituted by a methoxy group.

Compounds of formula 1 in which A—B is —CH₂—CHOH—, may be prepared e.g. by reduction of a cis- or trans-oxirane compound of the formula:

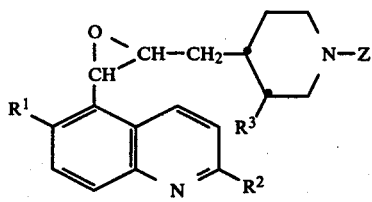

4 in which $R^1$, $R^2$ and $R^3$ are as defined above and Z is a protecting group and preferably benzyl, followed by removal of this protecting group in conventional manner. The reduction is suitable carried out by leading hydrogen gas through a suitable solvent, such as an alcohol, e.g. ethylalcohol, in the presence of a suitable catalyst, e.g. palladium on coal, at room temperature or slightly elevated temperature. As a result of the reduction generally alcohols are formed as a mixture of diastereoisomers, which may be separated in conventional manner. The removal of the protecting groups may be carried out with known techniques. If the protecting group is alkyl, this group may be removed e.g. with cyanogen bromide or chlorocarbonic acid ester. If the protecting group is a benzyl group, debenzylation occurs preferably catalytically.

The preparation of the cis- and trans-oxirane compounds of formula 4 has been described by L. Keefer, Thesis Univ. of New Hampshire 1966 and G. G. Lyle and L. K. Keefer, Tetrahedron 23, 3253-3263 (1976) or occurs in an analogous way. Generally, the compounds may suitably be prepared by quaternizing a compound of formula 2 in conventional manner, for example to the corresponding benzo bromide and converting the resulting compound with a base.

Because of the stereospecificy of the reaction a compound of formula 2 in the erythro configuration is preferably used as the starting material, while the quaternizing group is not too small, i.e. larger than methyl and ethyl. Thus, a suitable group is for example benzyl. The reaction with the quaternary compound is suitably carried out with a base, such as potassium hydroxide in a solvent, such as ethylalcohol.

It is noted, that if the above-described reaction is carried out with the quaternary salt of a threo compound of formula 2, a keto compound of the formula may be formed,

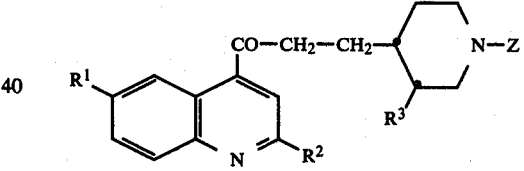

5 in which $R^1$, $R^2$, $R^3$ and Z are as previously defined. If a relatively small quaternary group is used, such as a methyl group, generally a keto compound of the formula 5 is formed in this reaction, both if a threo or an erythro compound of formula 6 is the starting material.

Threo compounds of formula 2 may also be converted to oxirane compounds of formula 4, if the quaternizing group is not too small, e.g. benzyl. This reaction is carried out with a strong base, in which the anion B⁻ is a bulky group, for example potassium t-butoxide in t-butanol. The resulting oxirane compound is usually in the cis-configuration.

The resulting compounds of formula 1, in which $R^1$, $R^2$ and $R^3$ are as previously defined and A—B is —CH₂—CHOH—, may be oxidized in conventional manner to the corresponding keto compounds, in which A—B is —CH₂—C(O)—. A suitable method includes the Oppenauer oxidation.

The starting compounds of formula 1, in which A—B is —C(NOR⁴)—CH₂— or —CH₂—C(NOR⁴)—, may be obtained for example by reacting the corresponding carbonyl compound with an O-substituted hydroxylamine derivative of formula R⁴O—NH₂, in which R⁴ is as previously defined. This reaction is carried out in conventional manner for this type of reaction. Preferably, the reaction is carried out in a solvent, such as an alcohol, dioxane, dimethyl formamide or pyridine, at a temperature generally between room temperature and the boiling point of the reaction mixture. The hydroxylamine derivative is usually added as an acid salt, preferably the hydrochloride, which salt is preferably dissolved in pyridine.

The starting materials which are necessary for the preparation of the compounds of the invention are known for the greater part. If necessary, they may be obtained in a manner known for the preparation of analogous compounds.

Compounds of formula 1 which possess an alkoxy group at the 6'-position and wherein $R^3$ is vinyl, are preferably converted to the corresponding 6'-hydroxy compounds with boron tribromide, which compounds may be converted in the same or another 6'-alkoxy compound in conventional manner, preferably with the aid of a mesyl ester. The 6'-alkoxy compounds in which $R^3$ is ethyl may be also converted to 6'-hydroxy compounds with 48% hydrobromic acid.

The reaction products obtained may be isolated from the reaction mixture and purified by conventional means.

In a number of cases, certain reaction steps may be carried out in a different sequence or simultaneously or without isolating intermediates, and these possibilities are all included in the invention.

Those skilled in the art will appreciate that protecting groups may be used to protect certain reactive functions during the above processes, in accordance with conventional chemical practice.

Certain compounds of formula 1 may also be used for the preparation of other compounds of formula 1 and are therefore also suitable as intermediates.

Diastereoisomers may be separated by known techniques, based on their different physical and chemical characteristics, e.g. by fractional crystallization or by column chromatography. These isomer separations may be effected after the final step of the synthesis used or optionally in a previous phase, after the formation of the mixture of diastereoisomers.

The free base and acid addition salt forms of the compounds of formula 1 may be interconverted by standard methods.

The compounds of formula 1 possess pharmacological activity. In particular they possess cardiovascular activity, for example anti-hypertensive, anti-thrombotic, vasodilatory and anti-arrhythmic activity.

An indicated suitable daily dosage (for a 70 kg human) is from 1 to 200 mg, of a compound of formula 1, preferably administered orally or parenterally in divided dosages of from 0,5 mg to 50 mg 2 to 4 times daily, or in retard form. Unit dose forms may thus contain 0.5, 1, 2.5, 10, 20, 25 or 50 mg or the like.

The compounds may be administered in free base form or in the form of their pharmaceutically acceptable acid addition salt forms, which salt forms have the same order of activity as the free base forms.

The compounds of formula 1 may be admixed with conventional pharmaceutically acceptable diluents or carriers. Optionally, other excipients may be added to facilitate administration for example in such forms as tablets, capsules and injectable solutions. The compounds may be also administered in combination preparations with other active agents.

The pharmaceutical compositions may be formulated in conventional manner, e.g. as for other anti-hypertensive agents.

The following Examples, which do not restrict the invention anyway, illustrate the invention.

EXAMPLE 1

2'-Methylhydrocinchonicine bifumarate (intermediate)

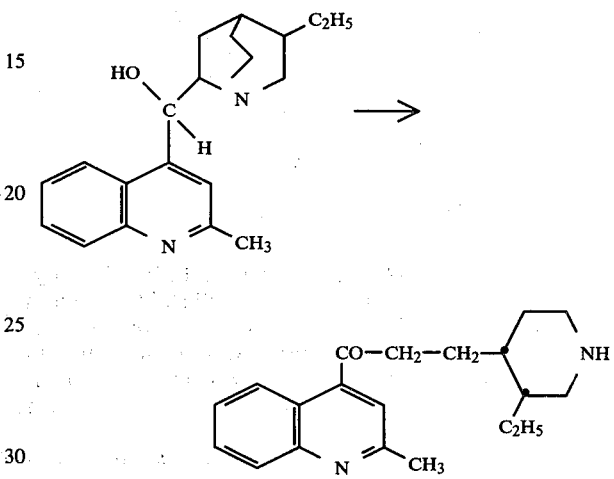

2'-Methylhydrocinchonidine, 167 g (538 mmol), was dissolved in 180 g (3 mol) of glacial acetic acid, after which 1500 ml of water were added. The mixture was refluxed for 48 h, and the conversion was followed by thin layer chromatography. After it was found that the reaction was substantially completed, the reaction mixture was poured on 500 g of ice, to which 100 g of sodium hydroxide were added. The mixture was then extracted three times with 250 ml of toluene, the layers were separated and the collected toluene fractions were dried over magnesium sulphate. The solution was filtered and concentrated in vacuo to a volume of about 250 ml. The solution was filtered over a short silica gel column with chloroform as the eluent. The fractions with the desired product were evaporated in vacuo, after which the resulting residue (145.6 g) was dissolved in 2500 ml of acetone, and 54.3 g (468 mmol) of fumaric acid were added. After heating and cooling the mixture the 2'-methyl-hydrocinchonicine was obtained as the bifumarate. Melting point 159°–160° C.

The base required for further conversion was obtained by dissolving the bifumarate in water, making the solution alkaline with 4 N sodium hydroxide (pH 9–10) and extracting it with toluene. After separating the layers the toluene layer was dried with molecular sieves, filtered and evaporated to dryness in vacuo. The base remained as an oil. In the same way the following compounds (intermediates) were prepared:

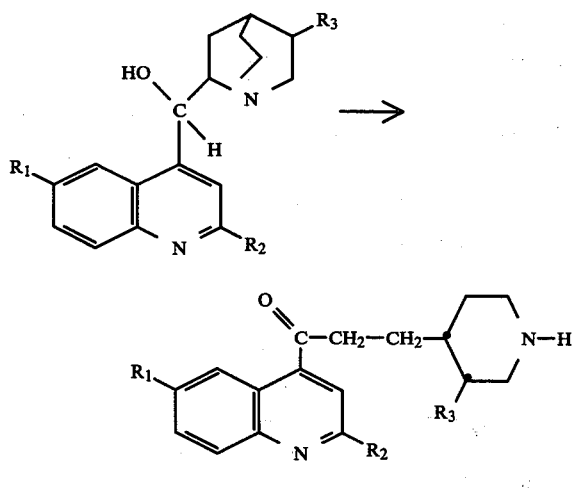

| Example | $R_1$ | $R_2$ | $R_3$ | m.p. °C./salt | |
|---|---|---|---|---|---|
| 2 | H | $CH_3$ | $CH=CH_2$ | 166-168 | BF |
| 3 | $OCH_3$ | $CH_3$ | $CH_2-CH_3$ | oil | |
| 4 | H | $(CH_2)_2-CH_3$ | $CH_2-CH_3$ | 148-152 | TO |
| 5 | H | $CH(CH_3)_2$ | $CH_2-CH_3$ | 97 | BO |

BF = bifumarate (mol. ratio 1:1)
TO = tetraoxalate (mol. ratio 1:2)
BO = bioxalate (mol. ratio 1:1)

EXAMPLE 6

6'-Isopentoxy-2'-methyl-hydrocinchonicine.bioxalate (intermediate)

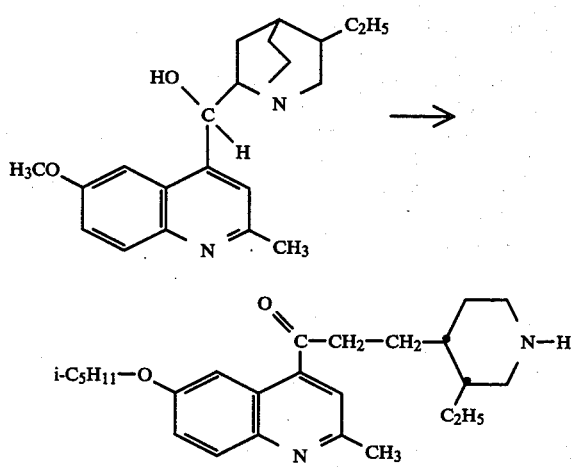

2'-Methylhydroquinine (21 g) was refluxed with 200 ml of 47% hydrobromic acid for 17 hours. After cooling and neutralizing with concentrated ammonia to pH 7-8, the 2'-methyl-6'-hydroxyhydrocinchonidine formed was extracted three times with 100 ml of chloroform. The chloroform fraction was evaporated in vacuo to dryness, after which the residue was dissolved in methyl ethyl ketone. An equivalent amount of hydrochloric acid, dissolved in isopropylalcohol was then added. After crystallization and recrystallization the 2'-methyl-6'-hydroxyhydrocinchonidine.hydrochloride was obtained, melting point 220°-222° C.

The product so obtained was suspended in 180 ml of n-pentanol, to which 8 g of potassium hydroxide were added. After stirring for 10 minutes 10.6 g of methane sulphonic acid isopentylester were added under nitrogen. The mixture was then heated at 40° C. for 30 hours while stirring. After the conversion was found to be substantially completed with the aid of thin layer chromatography, 90 ml of 2 N hydrochloric acid were added. The solvent was removed by steam distillation, after which sufficient 2 N sodium hydroxide was added to pH 12 and the resulting product was extracted three times with 100 ml of chloroform. The chloroform fraction was evaporated in vacuo to dryness, after which the crude 2'-methyl-6'-isopentoxy-hydrocinchonidine was obtained as an oil.

In the same way as described in Example 1 the obtained product was converted to 2'-methyl-6'-isopentoxy-hydrocinchonicine. Melting point of the bioxalate 154°-155° C.

EXAMPLE 7

2'-Propyl-hydrocinchonicinol-1

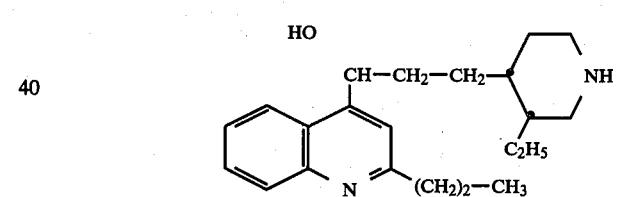

2'-Propylhydrocinchonicine (Example 4), 50 g (150 mmol) was dissolved in 225 ml of isopropylalcohol, after which the mixture was cooled to −10° C. A solution of 11.5 g (300 mmol) of sodium borohydride in 225 ml of isopropylalcohol was then added in such a way that the temperature did not exceed −5° C. The mixture was stirred for another 1 h at −10° C. till the conversion was substantially completed. The conversion was followed with thin layer chromatography. The mixture was then allowed to rise to room temperature, after which 250 ml of water was added. The mixture was extracted three times with 250 ml of chloroform. The collected chloroform fractions were evaporated at reduced pressure, which afforded the title compound as an oil. In the same way the following compounds were prepared:

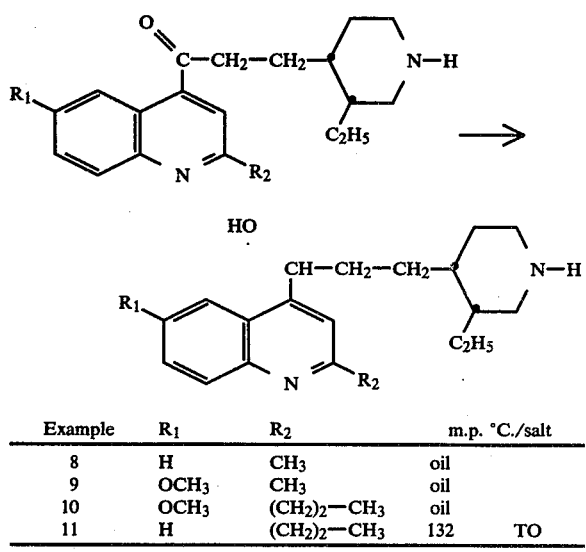

| Example | R₁ | R₂ | m.p. °C./salt |
|---|---|---|---|
| 8 | H | CH₃ | oil |
| 9 | OCH₃ | CH₃ | oil |
| 10 | OCH₃ | (CH₂)₂—CH₃ | oil |
| 11 | H | (CH₂)₂—CH₃ | 132 TO |

TO = tetraoxalate (mol. ratio 1:2)

EXAMPLE 12

2'-Methyl-desoxo-hydrocinchonicine.dihydrochloride

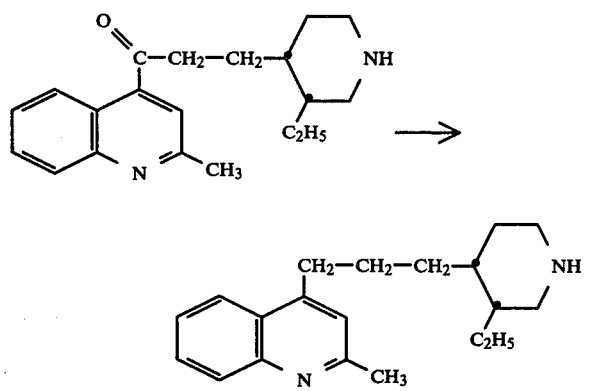

2'-Methylhydrocinchonicine (Example 1), 71 g (229 mmol), was dissolved in 200 ml of ethylene glycol, after which 20 ml 80% hydrazine hydrate were added. The mixture was heated till 140°–145° C. in a nitrogen atmosphere, and water was removed during 2 hours with a Dean-Stark apparatus. Then 30 g of potassium hydroxide were added to the reaction mixture in about 30 minutes, which caused evolution of nitrogen. After the addition of potassium hydroxide was completed the mixture was heated at 140° C. for another 2 hours. After cooling 250 ml of water were added, after which the mixture was extracted twice with 250 ml of toluene. The collected toluene fractions were washed twice with 250 ml of water and dried over molecular sieves. After filtration and evaporation at reduced pressure the crude reaction product was obtained, which was dissolved in 200 ml of methyl ethyl ketone. With the aid of an equivalent amount of hydrochloric acid, dissolved in isopropylalcohol, the 2'-methyldesoxohydrocinchonicine was obtained from this solution after heating and cooling, as its dihydrochloride. Melting point after recrystallization from methyl ethyl ketone: 192°–196° C.

EXAMPLE 13

6'-Isopentoxy-2'-methyl-desoxo-hydrocinchonicine

In the same way as described in Example 12. 6'-isoamyloxy-2'-methyl-hydrocinchonicine (Example 6) was converted into 6'-isoamyloxy-2'-methyl-desoxo-hydrocinchonicine. The compound was obtained as an oil.

EXAMPLE 14

2'-Methyl-hydrocinchonicine-O-methyloxime ether.bioxalate

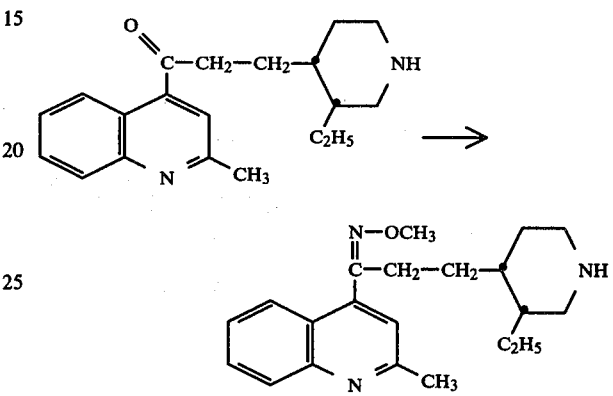

2'-Methylhydrocinchonicine (Example 1), 20 g (65 mmol) was dissolved in 200 ml of 96% alcohol, to which 7.6 g (92 mmol) of methoxylamine hydrochloride were added. The reaction mixture was refluxed for 16 hours, cooled and evaporated in vacuo. The residue was treated with 50 ml of concentrated ammonia and 100 ml of water, after which the formed product was extracted three times with 100 ml of chloroform. The chloroform fraction was evaporated in vacuo, after which the residue was dissolved in acetone. A calculated amount of oxalic acid was then added. After crystallization and recrystallization from acetone the title compound was obtained. Melting point 112°–114° C.

EXAMPLE 15

2'-Isopropyl-hydrocinchonicine-O-methyl oxime ether

In the same way as described in Example 14 but starting with 2'-isopropyl-hydrocinchonicine (Example 5), the title compound was obtained as an oil.

PHARMACOLOGY

Experiment 1—Effectiveness of the compounds of Examples in spontaneously hypertensive rats Systolic blood pressures were recorded by a modification of the tail cuff method described by I. M. Claxton et al. Eur. J.Pharmacology 37, 179 (1976). An oscilloscope or W+W BP recorder, model 8002, was used to display pulses.

Prior to all measurements rats were placed in a heated environment (33.5±0.5° C.) before transfer to a restraining cage. Each determination of blood pressure was the mean of at least 6 readings.

Spontaneously hypertensive rats (aged 12–18 weeks) with systolic blood pressures >170 mm Hg were considered hypertensive.

In the following table the results with certain compounds of the invention, which have been carried out with the above-described method, are mentioned. The numbers of the compounds correspond with those of the Examples.

| Compound No. | dosage mg/kg | change of systolic blood pressures (%) in different time intervals (h) | | | | |
|---|---|---|---|---|---|---|
| | | 1 | 2 | 4 | 6 | 24 |
| 12 | 100 | −4 | −2 | −9 | −7 | — |

Experiment 2—Effectiveness of the compounds of Examples in the

Guinea Pigs Electrostimulation Test

Arrhythmias are induced in guinea pigs by electrostimulation of the right ventricle of the heart. The animals are anaesthesized with urethane (1.2 g/kg i.p.) and artificially respirated before a needle electrode is inserted in the right ventricle of the heart. Substances are given intraduodinally 30 min. before the stimulation at a dose of 32 mg/kg.

The voltage needed for induction of extra systoles in control animals (n=6) is compared with that required for induction of arrhythmias in treated animals (n=6).

This method is based on the work of L. Szekeres and G. J. Papp. Naunyn-Schmiedebergs Arch. Exp. Path. Pharmak., 245, 70 (1963).

In the table the results of certain compounds of the invention are mentioned, which have been carried out according to the method described above.

The numbers of the compounds correspond with those of the Examples.

| Compound No. | Percent Increase in Voltage required for arrhythmia |
|---|---|
| 11 | 25 |
| 14 | 36 |

TOXICOLOGY

The compounds did not cause toxic signs at the doses used for the different tests.

We claim:

1. A compound of the formula

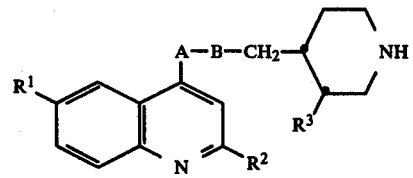

or a pharmaceutically acceptable salt thereof in which
A—B is —CHOH—CH$_2$—, —,
R$^1$ is hydrogen, hydroxy or lower alkoxy,
R$^2$ is lower alkyl, and
R$^3$ is ethyl or vinyl,
in which the configuration of the substituents in the 3- and 4-position of the depicted piperdine ring is cis.

2. A compound according to claim 1 having the formula:

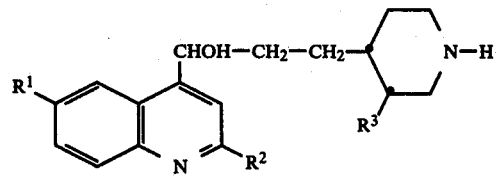

in which R$^1$, R$^2$ and R$^3$ are as therein defined.

3. A pharmaceutical composition comprising a cardiovascularly effective amount of a compound according to claim 1, or a pharmaceutically acceptable salt thereof, in combination with a pharmaceutically acceptable carrier.

4. The method of treating cardiovascular conditions in a human or other animal in need thereof which comprises administering an effective amount of a compound according to claim 1.

* * * * *